United States Patent [19]

von Bonin et al.

[11] Patent Number: 4,568,391

[45] Date of Patent: Feb. 4, 1986

[54] SIZING AGENTS

[75] Inventors: Wulf von Bonin, Leverkusen; Hans-Ulrich Buschhaus, Cologne; Ulrich Beck, Bornheim; Heinz Bäumgen, Leverkusen, all of Fed. Rep. of Germany

[73] Assignee: Bayer Aktiengesellschaft, Leverkusen, Fed. Rep. of Germany

[21] Appl. No.: 566,644

[22] Filed: Dec. 29, 1983

[30] Foreign Application Priority Data

Jan. 20, 1983 [DE] Fed. Rep. of Germany ....... 3301670

[51] Int. Cl.$^4$ .................... C09K 3/00; C07C 68/00
[52] U.S. Cl. .................... 106/287.24; 260/463; 162/158
[58] Field of Search .................... 260/1, 408, 463; 162/158; 106/287.24

[56] References Cited

U.S. PATENT DOCUMENTS

| 2,370,568 | 2/1945 | Muskat et al. | 106/179 |
| 3,275,674 | 9/1966 | Bottenbruch et al. | 260/463 |
| 3,930,932 | 6/1976 | Bjorklund | 162/158 |
| 4,459,239 | 7/1984 | Di Toro | 260/463 |

FOREIGN PATENT DOCUMENTS 2234716 2/1973 Fed. Rep. of Germany .
2459165 6/1976 Fed. Rep. of Germany .
1392746 4/1975 United Kingdom .

OTHER PUBLICATIONS

Chem. Abst.: 45:9269c, Kobbe, 1951.

*Primary Examiner*—Theodore Morris
*Attorney, Agent, or Firm*—Sprung, Horn, Kramer & Woods

[57] ABSTRACT

The invention provides new sizing agents, in particular for paper, which contain chloroformic acid esters of ester alcohols and/or carboxamide alcohols.

The chloroformic acid esters in question preferably have the following idealized structure:

$$(RCOX)_n R'(OCOCL)_m \qquad (I)$$

wherein
  X=an oxygen atom or an NH radical,
  R=an aliphatic, araliphatic or cycloaliphatic hydrocarbon radical having 8 to 28 carbon atoms,
  R'=the radical of an (n+m)-functional alcohol or amino alcohol having 2 to 10 carbon atoms, where the functionality refers to the total number of OH and NH$_2$ groups,
  n=an integer from 1 to 4, and
  m=an integer from 1 to 3.

8 Claims, No Drawings

SIZING AGENTS

The invention relates to new sizing agents, in particular for paper, which are based on chloroformic acid esters.

The reactivity of chloroformic acid esters has been known for a long time, for example the fact that chloroformic acid esters react with OH groups, in the presence or absence of acid acceptors, to give, in many cases, carbonates. The reaction can take place with primary and secondary OH groups, in particular aliphatic OH groups of the type present in carbohydrates, for example in starch or cellulose.

Attempts have indeed been made to utilise this knowledge about how chloroformates react by using, for the reactive sizing of papers, chloroformic acid esters of the formula RO—COCL, where the R used was hydrocarbon radicals having 8 to 40 carbon atoms, such as long-chain aliphatic radicals, cholesteryl radicals, and the like. On this point, see, for example, Germain Auslegeschrift No. 2,234,716.

These products, however, have certain disadvantages, either as regards accessibility, for example in the case of the cholesteryl component, or, in particular, as regards the insufficient stability of aqueous formulations of the reactive chloroformic acid esters of simple fatty alcohols. Moreover, higher fatty alcohols, unlike the fatty acids, are relatively inaccessible starting products.

It has now been found, surprisingly, that these disadvantages can be avoided as a whole by using, as sizing agents, not chloroformic acid esters of hydrocarbon alcohols (i.e. for example of fatty alcohols), but those of ester alcohols and/or of carboxamide alcohols.

The chloroformic acid esters used for the new sizing agents for paper preferably have the following idealised structure:

$$(RCOX)_nR'(OCOCL)_m \quad (I)$$

wherein
X=an oxygen atom or an NH radical,
R=an aliphatic, araliphatic or cycloaliphatic hydrocarbon radical having 8 to 28 carbon atoms,
R'=the radical of an (n+m)-functional alcohol or amino alcohol having 2 to 10 carbon atoms, where the functionality refers to the total number of OH amd NH₂ groups,
n=an integer from 1 to 4, and
m=an integer from 1 to 3.

In the formula (I), X preferably represents oxygen, R preferably represents a hydrocarbon radical having 11 to 20 carbon atoms, R' preferably contains 3 to 6 atoms, n preferably denotes 2 or 3, and m preferably denotes 1 or 2.

These chloroformic acid esters have a good sizing action, can be formulated in an aqueous medium, tend to be much stabler than the chloroformic acid esters of simple fatty alcohols, and derive from readily accessible fatty acids.

Of the processes those skilled in the art will know for preparing chloroformic acid esters, the process of reacting OH-containing starting materials with phosgene is preferably used for preparing the sizing agents according to the invention. The preparation of chloroformic acid esters by processes of this type corresponds to the state of the art, so that they are readily accessible. This also applies to the preparation of the fatty acid amide alcohols to be converted into chloroformic acid esters, in particular to the fatty acid ester alcohols which are preferably used and which can be readily prepared, for example by reacting fatty acids, in particular technical fatty acid mixtures, having melting points above 30° C. with polyalcohols, if appropriate in a vacuum or under an inert gas at temperatures between 100 and 250° C. while driving off the water of reaction.

The preparation of the chloroformic acid esters can be systematically represented as follows:

(A) Preparation of chloroformic acid esters (I) with X=O:

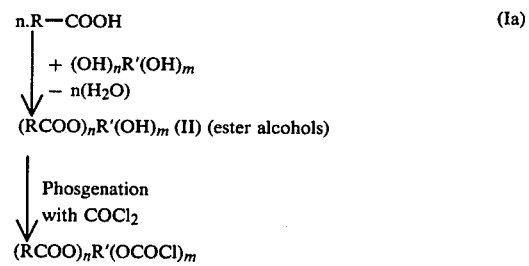

(B) Preparation of chloroformic acid esters (I) with X=NH:

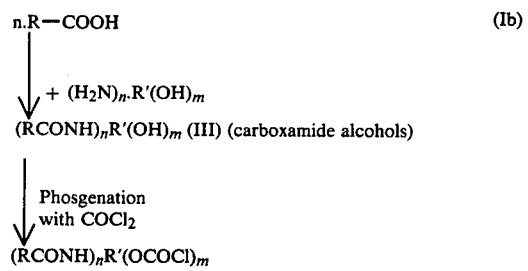

wherein R, R', m and n have the meaning given under formula (I).

For sizing purposes the chloroformic acid esters can be formulated in the form of a solution or suspension in non-aqueous media, such as alcohol, acetone, petrol, toluene, trichloroethylene, readily melted or liquid emulsifiers, all dispersants, or preferably in the form of an aqueous suspension or dispersion by means of emulsifying and/or dispersing auxiliaries, as, for example, in the case of the stearyldiketene formulations known to those skilled in the art. These aqueous formulations also take advantage of the advantageous storage properties of the new, chloroformate-based sizing agents.

The sizing agents according to the invention can themselves contain further sizing-active substances in addition to the chloroformates or can be used jointly or mixed with other sizing agent formulations.

The n+m-functional alcohols which are preferably used alone or mixed with one another are ethylene glycol, propylene glycol, neopentyl glycol, butanediol, hexanediol, glycerol, trimethylolpropane, pentaerythritol, sorbitol and other sugar alcohols, in particular glycerol and in particular trimethylolpropane.

The n+m-functional amino alcohols which are preferably used alone or mixed with one another are ethanolamine, diethanolamine, triethanolamine, propanolamine, dipropanolamine, tripropanolamine (in the n and iso forms), N-alkyl-diethanolamines, (N-dialkylamino)- alkyl-diethanolamines and adducts of 1–4 mols of ethylene oxide and/or propylene oxide on ethylenediamine.

R radicals of the (RCO—) grouping and having 8-28 C atoms are preferably to be understood as meaning those which can be derived from fatty acids or fatty acid mixtures having melting points above 30° C., such as tallow fat acids, coconut fat acids, tall fat acids, resin acids, palmitic acids, behenic acids or, in particular, stearic acid and mixtures containing stearic acid.

According to the invention, preferred chloroformic acid esters are those which have melting points above 10° C., preferably between 20° and 60° C.

The chloroformic acid esters can also be used in their unpurified technical preparation form.

The chloroformic acid esters are used in active ingredient contents of 1–30, preferably 3—15, % by weight in, if appropriate, anionic or more likely non-ionic, but in particular cationic, aqueous formulation.

The aqueous sizing agent formulations are preferably emulsions or dispersions of the chloroformic acid esters according to the invention and can be further diluted for use to active ingredient concentrations of less than 1 percent by weight and may be combined with other sizing agents, further paper auxiliaries, such as optionally modified starches, fillers, dyestuffs, fluorescent brighteners, retention aids, fixing aids, wet-strength agents and the like.

The new sizing agents may be used on the surface of the paper but are especially used in the paper pulp.

Suitable non-aqueous formulations are in general fluent or even free-flowing solid formulations, melts of the chloroformic acid esters or mixtures thereof, mixtures with other sizing agents or dispersing auxiliaries, or even solutions in water-miscible or non-water-miscible solvents or solvent mixtures with active ingredient contents of about 3 to about 75% by weight. Also suitable are dispersions in non-aqueous solvents or dispersing media, for example in ethanol, isopropanol, butanol, toluene, trichloroethylene, acetone, ethyl acetate, glycol methyl ether, glycol methyl ether acetate, petrol fractions, petroleum distillates containing aliphatics, naphthenes, aromatics and the like, animal and vegetable oils, or mixtures of these auxiliaries.

The aqueous formulations are prepared in the presence of, optionally, mixtures of anionic, in isolated cases, but preferably non-ionic or in particular cationic low molecular weight, oligomeric or polymeric wetting-emulsifying or dispersing auxiliaries at temperatures preferably just above the melting point of the chloroformic acid esters by means of customary state of the art emulsifying equipment, such as, for example, stirrers or rotor-stator, nozzle or ultrasonic equipment, followed by cooling as rapidly as possible to below the crystallite melting point, or lower, as the case may be, for example to temperatures around 4° C.

Possible auxiliaries for preparing the aqueous dispersions are, for example, the groups of substances with which those skilled in the art are familiar and having wetting, emulsifying, dispersing or stabilising properties, and although their amounts, relative to chloroformate, should be kept as low as possible, they can, when they themselves have sizing characteristics, exceed the amount of the chloroformate contained in the formulation by a number of times.

In the case where the auxiliaries added have no sizing characteristics or have characteristics which, in principle, impair the sizing action, their level, relative to chloroformate, should be less than 80% by weight, preferably between 2 and 50% by weight.

In the case where the substances which are used as dispersing auxiliaries can themselves have sizing characteristics or even themselves are sizing agents or sizing agent formulations, the chloroformic acid esters to be used according to the invention can of course also be present in the aqueous formulation in much lower proportions of the total active ingredient with sizing action, i.e. they can be used as additives to other sizing components.

Dispersing auxiliaries with sizing agent characteristics can be understood herein as meaning the following as such or in the form of their aqueous formulations: quaternised or non-quaternised basic polymers, oligomers, fatty acid amides, starches, colophony or hydrocarbon resins or even, in principle, sizing agents which have no basic groups but are in the form of a cationic or non-ionic aqueous formulation and are based on tall-resin, fatty alkyl diketene products, hydrocarbon resins or colophony resins or wool fats. Possible dispersing auxiliaries without their own sizing actions are, for example, such cationic polyadducts or oligoadducts, polycondensates or oligocondensates as are known in paper technology for use as sizing improvers, retention aids or wet-strength agents, starch, cationic starches, celluloses, chitin products, resin acid derivatives or other cationically modified polysaccharides or oligosaccharides of, usually, vegetable origin, if appropriate combined with ionic surfactants, for example naphthalenesulphonates, ligninsulphonates, alkyl sulphates, fatty acid salts, quaternary fatty ammonium salts or, in particular, non-ionic state of the art surfactants, be they quaternary, aliphatic or araliphatic ammonium compounds, alkoxylated resin acids, fatty acids, fatty alcohols, isononylphenols, lecithins, proteins or fats, or carbohydrates and the like.

The new sizing agents are used in the form of their formulations for surface-finishing or preferably pulp-finishing papers. The aqueous formulations have active ingredient contents in the form of sizing agent of 1 to 30, preferably 3 to 15, % by weight. Before use in the paper pulp or sizing liquor they can be diluted still further, for example down to active ingredient contents of 0.1 to 1%.

The new sizing agents have the advantage of being much stabler in the form of their aqueous formulations than the chloroformic acid esters of simple fatty alcohols, while, nevertheless, still having reactive groups which can evidently still react so efficiently with the paper stuff as to develop, immediately after the drying of the paper even at relatively low temperatures, for example around 80° C., and which, for example, epichlorohydrin reaction products or fatty alkyl diketene sizing agents respond only slowly, if at all, their full sizing action, i.e. they effect immediate sizing which can be assessed immediately after the paper machine.

There is no need to add alum or other paper auxiliaries, although an addition of such auxiliaries, for example those based on cationic starch, quaternised polyamines, quaternised polyamide-amines, quaternised basic formaldehyde resins, methylcellulose, carboxymethylcellulose, ligninsulphonic acids, starches and polysaccharides of most diverse origins, xanthene, pullulan, chitosam, polymers or copolymers of (meth)acrylic acid, maleic, fumaric or itaconic acids or other polymers and copolymers having carboxyl or sulphonic acid groups which can be in salt form, collagen, gelatin, alginates and caragenates, should be contemplated and is possible if so desired. It is similarly possible to effect combinations with lightweight fillers, microcapsules, soluble and insoluble dyestuffs or other paper-additives. The effectiveness of the new sizing agents is not impaired by fluorescent whiteners.

The sizing agents are particularly highly suitable on their own or combined with other sizing agents, for pulp-sizing paper, but they can also be used, if so desired, for surface-sizing. They cannot only be used on chalk-containing or possibly even kaolin-containing papers, but also on those which contain no filler or a filler of a different type, such as, for example, talcum or gypsum. They are similarly suitable for sizing cellulosic materials, such as board, synthetic pulps, textile materials, leather, cardboard or woodchip boards or insulating sheets.

The following examples are intended to illustrate the invention; the parts and percentages therein are by weight, unless otherwise stated.

PREPARATION EXAMPLES

The chloroformates are prepared by condensing 1 mole of n+m-functioned alcohol and n moles of technical fatty acid under nitrogen and driving off the water of condensation at 170° C. in the course of 10 hours. The resulting ester alcohol has an acid value of less than 12 and is phosgenated in a solution in toluene, and the chloroformic acid ester is isolated by distilling off the toluene.

The chloroformic acid esters which are used herein all melt above 25° C. and below 50° C.

The comparative substance used is a material prepared by analogous phosgenation of stearyl alcohol.

The following names are used:
Comparative active ingredient
  Basis: stearyl alcohol
Active ingredient A
  Basis: 1 mole of glycerol, 2 moles of technical coconut fat acid
Active ingredient B
  Basis: 1 mole of trimethylolpropane, 2 moles of technical stearic acid.

The following dispersing auxiliaries were used:
Auxiliary A
  Copolymer of 30% N-(3-dimethylaminopropyl)-maleinimide, 10% styrene and 60% butyl acrylate, quaternised with epichlorohydrin (Example 17 of German Offenlegungsschrift 3,046,981).
Auxiliary B
  Commercially available cationic starch
Auxiliary C
  Dimethyloleylbenzylammonium chloride in water
Auxiliary D
  Polyvinyl alcohol
Auxiliary E
  Amide of 2 moles of oleic acid and 1 mole of triethylenetetramine, reacted with about 3 moles of epichlorohydrin.

The emulsifying equipment used was a rotor-stator emulsifying unit (Megatron from Kinematica GmbH).

The aqueous sizing agent formulations were prepared by, first of all, setting the water in a mixture with the auxiliaries in circulation at 50° C. in the mixing unit. The chloroformate was then added in the form of the preheated melt at 50° C. at 90% of the maximum speed (9,000 r.p.m.), and the mixture was circulated at 50° C. for 1 minute, the circulating volume being 200 ml. The mixture was then cooled down to 18° C. in the course of 3 minutes, and the resultant stable emulsion was used as a sizing agent; the particle diameters of the emulsion were between about 1.5 and 100 $\mu$m.

It is a significant advantage of reactive sizing agents that they are reactive on alum-free and chalk-containing papers, on which resin size is not very effective. The sizing agents according to the invention are therefore also tested on, for example, alum-free, chalk-containing paper.

5 g of a mixture of 50 g of pinewood sulphite pulp, 50 g of beechwood sulphate pulp and 25 g of chalk are suspended in 200 ml of tapwater. x% of the sizing agent (active ingredient relative to cellulose plus filler) are then added with stirring. The mixture is then bulked to about 1 liter with water and without adding a fixing agent, and the sheet of paper is prepared on a sheetformer. The sheet of paper is sucked off, pressed and dried on a drying cylinder at 110° C. in the course of 5 minutes. Strips (2 cm×6 cm) are then cut out of the sheet for the ink flotation test.

The ink flotation test is used as a criterion for assessing the sizing agents: strips of paper finished with the agent to be tested are laid on the surface of a dish filled with standard DIN 53,126 ink, and the time is measured until the ink strikes through the paper to the side facing the observer.

With a standardised procedure this test provides a very good way of assessing various sizing agents.

Another way of assessing is to determine the water absorption on the papers by the DIN 53,132 (November 1965) Cobb method, after a 60-second exposure: the lower the measured water absorption (Cobb value), the better is the sizing action of the sizing agent.

The illustrative examples have been condensed into the following table, together with the assessments:

|  | Example No. | | | | | | | | | | |
| --- | --- | --- | --- | --- | --- | --- | --- | --- | --- | --- | --- |
|  | 1 | 2 | 3 | 4 | 5 | 6 | 7 | 8 | 9 | 10 | 11 |
| Active ingredient type; % | Comparison; 6 | → | → | → | B; 6 | → | → | → | A; 6 | A; 12 | → |
| Auxiliary type; % | A; 2 | → | → | → | A; 2 | → | → | → | B; 1 | A; 2 | → |
| Auxiliary type; % |  |  |  |  |  |  |  |  | C; 1 |  |  |
| Auxiliary type; % |  |  |  |  |  |  |  |  |  | D; 0.5 |  |
| Auxiliary type; % |  |  |  |  |  |  |  |  | E; 1 |  |  |
| Amount of water; % | 92 | → | → | → | 92 | → | → | → | 91 | 85.5 | → |
| Exposure at 20° C. (hours) | 3 | 60 |  |  | 3 | 240 |  |  |  | 3 |  |

-continued

| | Example No. | | | | | | | | | | |
|---|---|---|---|---|---|---|---|---|---|---|---|
| | 1 | 2 | 3 | 4 | 5 | 6 | 7 | 8 | 9 | 10 | 11 |
| Exposure at 8° C. (days) | | | 3 | 10 | | | 10 | 100 | 10 | | 100 |
| Level (% of active ingredient) | 0.3 | 0.3 | 0.3 | 0.3 | 0.3 | 0.3 | 0.3 | 0.3 | 0.3 | 0.3 | 0.3 |
| Ink time (approximate, in seconds) | 800 | * | 200 | <10 | 850 | 320 | 840 | 705 | 415 | 930 | 825 |
| Cobb value | 21 | * | 86 | 100 | 25 | 55 | 25 | 27 | 32 | 21 | 25 |

*Dispersion broke and solidified
In all the examples, the papers were immediately sized on drying.
Measurements after 1, 3 or 6 days show no late reaction of chloroformic acid ester formulations.
The "→" symbol denotes that the entry in the column on the left applies in each case.

The experiments listed in the table show that the new chloroformic acid ester sizing agents are much more stable in an aqueous medium than the simple chloroformic acid esters based on fatty alcohol, and that there are very different formulating options.

EXAMPLE 12

30 parts by weight of an addition product of 10 moles of ethylene oxide on isononylphenol, which has been cyanoethylated at the OH group, are added to 70 parts by weight of active ingredient B, which has a melting range from 25° to 33° C. A readily fluent solution forms. This solution is used as a non-aqueous sizing agent formulation by adding it in an amount of 0.3% (in the form of the active ingredient contained therein), with stirring, to the chalk-containing paper stuff, wherein the sizing agent becomes well dispersed. A paper sample prepared and tested by the method used in Examples 1-11 has a Cobb value of 29.5. The advantage of formulations of this type is that they are naturally easily metered as a liquid and that they can be stored for as long as desired, because of the absence of water.

EXAMPLE 13

The unsized chalk-containing experimental paper is dipped into a 0.15% strength toluene solution of active ingredient type B for one second, is then squeezed between filter paper discs under 1 kg/cm², and is heated in a water-saturated atmosphere at 100° C. for 3 minutes. After the paper which has been surface-treated in this way has been conditioned at room temperature, its ink flotation time is measured as 650 seconds.

We claim:

1. Sizing agents, characterised in that the sizing agent formulation contains chloroformic acid esters of the following idealised structure:

$$(RCOX)_n R'(OCOCL)_m \qquad (I)$$

wherein
X = an oxygen atom or an NH radical,
R = an aliphatic, araliphatic or cycloaliphatic hydrocarbon radical having 8 to 28 carbon atoms,
R' = the radical of an (n+m)-functional alcohol or amino alcohol having 2 to 10 carbon atoms, where the functionality refers to the total number of OH and NH$_2$ groups,
n = an integer from 1 to 4, and
m = an integer from 1 to 3.

2. Sizing agents according to claim 1, characterised in that in the formula I
X = an oxygen atom,
R = a hydrocarbon radical having 11 to 20 carbon atoms,
R' = a radical of an (n+m)-functional alcohol having 3 to 6 carbon atoms,
n = 2 or 3 and
m = 1 or 2.

3. Sizing agents according to claim 1, characterised in that the chloroformic acid esters contained therein have melting points between 10° and 60° C.

4. Sizing agents according to claim 1, characterised in that the RCO grouping of the formula I derives from fatty acids or fatty acid mixtures having melting points above 30° C., and R' derives from trimethylolpropane.

5. Sizing agents according to claim 1, characterised in that m = 1.

6. Sizing agents according to claim 1, characterised in that the chloroformic acid esters are used in the form of their technical crude products.

7. Sizing agents according to claim 1, characterised in that the chloroformic acid esters are used in a combination or admixture with further components having a sizing agent function.

8. Sizing agents according to claim 1, characterised in that the chloroformic acid esters are used in the form of aqueous formulations.

* * * * *